United States Patent [19]

Kent

[11] Patent Number: 4,879,070

[45] Date of Patent: * Nov. 7, 1989

[54] PRODUCTION OF FORMATE SALTS

[75] Inventor: Alexander G. Kent, North Humberside, England

[73] Assignee: BP Chemicals Limited, London, England

[*] Notice: The portion of the term of this patent subsequent to Oct. 2, 2001 has been disclaimed.

[21] Appl. No.: 180,672

[22] Filed: Apr. 7, 1988

Related U.S. Application Data

[63] Continuation of Ser. No. 946,667, Jan. 5, 1987, abandoned, which is a continuation of Ser. No. 689,826, Jan. 9, 1985, abandoned.

[30] Foreign Application Priority Data

Jan. 14, 1984 [GB] United Kingdom ............... 8401005

[51] Int. Cl.$^4$ .............. C07C 87/08; C07C 87/10; C07C 87/12; C07C 87/123

[52] U.S. Cl. ............................ 562/550; 562/609

[58] Field of Search ......................... 260/501.1

[56] References Cited

U.S. PATENT DOCUMENTS

| | | | |
|---|---|---|---|
| 1,019,230 | 3/1912 | Bubusc et al. | 260/501.1 |
| 3,959,386 | 5/1976 | Pinke | 568/909 |
| 4,474,959 | 10/1984 | Drury et al. | 260/501.1 |

Primary Examiner—J. E. Evans
Attorney, Agent, or Firm—Brooks Haidt Haffner & Delahunty

[57] ABSTRACT

Formate salts of nitrogenous bases containing a tertiary nitrogen atom are prepared by reacting the nitrogenous base with carbon dioxide and hydrogen in the presence of a solvent and a catalyst comprising an inorganic or organometallic compound of rhodium and an organophosphorus compound. The catalysts disclosed effect the reaction at a lower temperature and at higher productivities relative to the Group VIII metal catalysts of the prior art.

15 Claims, No Drawings

PRODUCTION OF FORMATE SALTS

This application is a continuation, of application Ser. No. 946,662, filed Jan. 5, 1987, now abandoned which is a continuation of application Ser. No. 689,826, filed Jan. 9, 1985, now abandoned.

The present invention relates to a process for the production of formate salts of nitrogenous bases containing tertiary nitrogen atoms.

Trialkylammonium formates have been used in the reduction of carbonyl compounds [Kataoka, Shinji; Tabata, Masayoshi; Takata, Yoshiyuki; Hokkaido Daigaku Kogakubu Kenkyu 1972 (63), 145–51 (Japan)], as catalysts in the production of monoalkyl ethers of trimethyleneglycol (USSR Pat. No. 495300), and in the production of polyurethane foams from resole polyols (U.S. Pat. No. 4293658) and in various other applications. They are generally produced by reacting formic acid with the appropriate tertiary amine.

Japanese patent publication No. 53-46820 describes the production of formic acid and its esters by reacting a compound of formula ROH (wherein R is either hydrogen or a hydrocarbon group) with carbon dioxide and hydrogen in the presence of, as catalyst low valent and/or hydride complexes of Group VIII transition metals and basic materials containing alkali metals and alkaline earth metals. The specification teaches that using water as solvent the product is formic acid and using an alkanol as solvent the prodcut is an ester of formic acid.

Japanese patent publication No. 53-46816 describes the production of formic acid and its esters by a similar reaction to that described in publication No. 53-46820 except that instead of an inorganic base there is employed an organic base which is an aliphatic tertiary amine.

Japanese patent publicaton No. 53-46818 describes the production of alkali metal formates by reacting alkali metal carbonates with carbon dioxide and hydrogen.

Finally our European Application No. 83 302845.9 describes the production of trialkylammonium salts of formic acid by reacting nitrogenous bases containing tertiary nitrogen atoms with carbon dioxide and hydrogen in the presence of a compound of a Group VIII transition metal.

We have now found that formate salts of nitrogenous bases containing tertiary nitrogen atoms can be produced by reacting carbon dioxide and hydrogen in the presence of a nitrogenous base in alcoholic or aqueous alcoholic media using as catalyst a compound comprising 1. an inorganic or organometallic compound of rhodium, and
2. an organophosphorus compound.

The rhodium/organophosphorus catalysts as described herein show two major advantages over the catalysts described in application No. 83.302845.9. Firstly, the rhodium/organophosphorus catalysts effect reaction at a lower temperature than comparable ruthenium catalysts and secondly, the rhodium/organophosphorus catalysts also cause an increase in the productivity of trialkylammonium formate at comparable temperature.

Accordingly, the present invention provides a process for the production of a formate salt of a nitrogenous base containing a tertiary nitrogen atom which process comprises reacting hydrogen and carbon dioxide with the nitrogenous base containing a tertiary nitrogen atom in the presence of a solvent and an effective amount of a catalyst characterised in that the catalyst comprises an inorganic or organometallic compound of rhodium and an organophosphorus compound.

The carbon dioxide may either be carbon dioxide itself, which is widely available on an industrial scale, or a carbonate or a bicarbonate or a mixture thereof. Carbon dioxide may be used as a gas or as a liquid or as a solid, preferably as a gas. Using carbon dioxide gas as the source of carbon dioxide it is preferred to use partial pressures of carbon dioxide and hydrogen which are as high as is practicable and economic. The use of high partial pressures of hydrogen is desirable because the reaction rate and yield of the formate salt increase as the partial pressure increases. The partial pressure of carbon dioxide is less critical but suitably the carbon dioxide partial pressure may be up to 60 bar and the hydrogen partial pressure up to 250 bar. Small amounts of impurities in the carbon dioxide and hydrogen can be tolerated.

Suitably the partial pressure of carbon dioxide is from 10 to 50 bar and that of hydrogen from 10 to 150 bar. The ratio of the partial pressure of hydrogen to that of carbon dioxide is preferably at least 1:1 more preferably at least 1.5:1.

The nitrogenous base containing a tertiary nitrogen atom may suitably be of formula:

or of formula:

wherein in the formulae, $R^1$, $R^2$ and $R^3$, which may be the same or different, are hydrocarbyl groups or substituted hydrocarbyl groups or any two or all of $R^1$, $R^2$ and $R^3$ may form part of a ring, $R^4$ is a hydrocarbyl group or substituted hydrocarbyl group and $R^5$ is a divalent organic group or $R^4$ and $R^5$ may form part of a ring. Suitably the hydrocarbyl group is an aliphatic, cycloaliphatic, aryl or alkaryl group. Substituted hydrocarbyl groups may contain for example nitrogen or oxygen. Preferably the nitrogenous base containing a tertiary nitrogen atom is a trialkylamine, even more preferably a lower trialkylamine, for example a $C_1$ to $C_{10}$ trialkylamine. Examples of suitable trialkylamines are trimethylamine, triethylamine, tripropylamine and tributylamine. Examples of other nitrogenous bases which may be employed are amidines, e.g. 1,8-diazobicyclo[5.4.0]undec-7-ene (DBU) and 1,4-diazobicyclo[2.2.2]octane (DABCO), pyridines and picolines. Mixtures of nitrogenous bases may be used if so desired. The nitrogenous base containing a tertiary nitrogen atom is suitably added in amounts which produce a concentration in the range 1 to 50 mole % based on the total reaction mixture.

The formate salt produced byt he present process comprises a formate anion and a cation derived from the nitrogenous base by protonation. Thus, for exaple when the nitrogenous base used is triethylamine, the formate salt produced is triethylammonium formate.

As solvent there may be used either one or more alcohols or a mixture of one or more alcohols with water. Suitable alcohols include methanol, ethanol, propanols, butanols, glycols and polyols. We have found that using secondary alcohol/water mixture a product consisting substantially exclusively of the formate salt can be produced whereas using other alcohols and alcohol/water mixtures there may be produced, in addition to the formate salt, formate esters. Of the secondary alcohol/water mixtures the use of isopropanol/water mixtures can lead to advantages in terms of rate and yields. It is therefore preferred to use as the solvent a mixture of isopropanol and water. Preferably isopropanol comprises from 20 to 80, even more preferably from 30 to 70, mole percent of the isopropanol/water mixture.

In addition or as an alternative to a secondary alcohol a glycol may be suitably used. Preferred glycols include ethylene glycol, diethylene glycol, triethylene glycol, tetraethylene glycol, propylene glycol and the like.

With regards to the metal component of the catalyst, any source of rhodium may be used. Rhodium may be added in any convenient form whether soluble or insoluble in the initial solution. Thus the rhodium may be added in the form of a simple salt such as the halide, nitrate, sulphate or acetylacetonate or in the form of an organometallic rhodium complex or as the metal. Suitably the catalyst concentration may be in the range of 50 to 4,000, preferably 200 to 1,000 parts per million by weight.

With regard to the organophosphorus component a range of compounds may be used. Phosphines of the formula

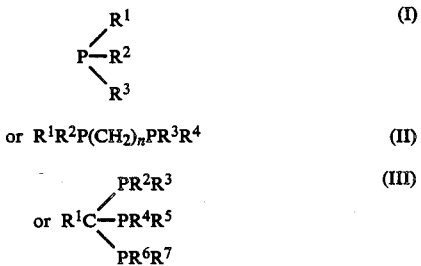

or $R^1R^2P(CH_2)_nPR^3R^4$      (II)

or $R^1C\overset{PR^2R^3}{\underset{PR^6R^7}{-PR^4R^5}}$      (III)

may suitably be used wherein n=1 to 10 and wherein $R^1$ and $R^7$ are individually hydrocarbyl groups containing from 1 to 20 carbon atoms. In addition any two of $R^1$ to $R^7$ may together form an organic cyclic ring system bound to phosphorus. The hydrocarbyl groups may be substituted or unsubstituted aliphatic groups or cycloaliphatic groups or unsubstituted or substituted aromatic groups. Examples of suitable compounds having the formula (I) are tri-n-butylphosphine, triphenylphosphine and tricyclohexylphosphine. An example of (II) is 1,2-diphenylphosphinoethane, $(C_6H_5)_2P(CH_2)_2P(C_6H_5)_2$ and an example of (III) is $CH_3C(P(C_6H_5)_2)_3$.

Preferred examples of the organophosphorus compound are triphenylphosphine and tri-n-butylphosphine.

It will be appreciated by those skilled in the art that some or all of the two components of the catalyst may be added as a single compound; for example a phosphine complex of rhodium. An example of such a compound is tris(triphenylphosphine) rhodium chloride $RhCl(P(C_6H_5)_3)_3$.

The preferred ratio of organophosphorus component to the rhodium component is 3 to 1.

The process may suitably be operated at a temperature in the range from 15° to 200° C. preferably from 30° to 120° C.

The process may be carried out batchwise or continuously.

The formate salt produced by the present invention may be subsequently separated from the reaction mixture, for example by distillation. The recovered formate salt can then subsequently be converted into formic acid using for example the method described in European patent application No. 126524A.

The invention will now be described by reference to the following Examples. In these Examples, the rate of reaction refers to the rate of production of the formate salt (moles/hr) divided by the weight of reaction solution (Kgs). The conversion to formate salt was calculated according to the following equation $$\frac{\text{moles of formate produced}}{\text{moles of nitrogenous base added}} \times 100 = \text{conversion}$$

Examples 14 and 16 does not constitute part of the invention as herein described but are included for the purpose of comparison.

EXAMPLE 1

A 300 ml capacity stainless steel autoclave, fitted with a rotary stirrer, was charged with 101.5 g of isopropanol, 19.5 g of water, 0.152 g rhodium trichloride, 0.456 g triphenylphosphine and 28.2 g of triethylamine. The autoclave was closed and carbon dioxide was introduced when a steady pressure of 27 bars was reached. The autoclave was then heated to 40° C. and hydrogen introduced to give an initial total pressure of 80 bars. At the end of the reaction period the autoclave was cooled to room temperature and the excess pressure discharged. A sample of the liquid reaction product was then taken, hydrolysed with 5M hydrochloric acid and analysed by gas-liquid chromatography for formic acid. The rate of reaction was 1.4 mol/kg/h and the conversion to triethylammonium formate was 81%.

EXAMPLE 2

This example shows that the rhodium component and the organophosphorus component may be added as single rhodium-phosphine compound.

The method of Example 1 was followed except that the autoclave was charged with 101.7 g of isopropanol, 19.5 g of water, 0.575 g of tris(triphenylphosphine) rhodium (1) chloride $(RhCl(P(C_6H_5)_3)_3)$ and 28.2 g of triethylamine. In this example the rate of reaction and conversion to triethylammonium formate were 4.2 mol/kg/h and 70% respectively.

EXAMPLE 3

This example shows that tri-n-butylphosphine is a suitable organophosphorus component.

The method of Example 1 was followed except that the autoclave was charged with 101.5 g of isopropanol, 19.5 of water, 0.152 g of rhodium trichloride, 0.353 g of tri-n-butylphosphine and 28.2 g of triethylamine. The rate of reaction and conversion to triethylammonium formate were, in this example, 0.6 mol/kg/h and 71% respectively.

EXAMPLES 4-9

These example show that amines other than triethylamine may be used in order to carry out this invention.

The method of Example 1 was followed and the autoclave charged with 101.5 g of isopropanol, 19.5 g of water, 0.152 g of rhodium trichloride, 0.456 g of triphenylphosphine and the appropriate amount of amine (Table 1). The rates of reaction and conversions to the appropriate formate, for each example, are given in Table 1.

TABLE 1

| Example | Amine | Amount of Amine (g) | Reaction Rate (mol/kg/h) | Conversion (%) |
|---------|-------|---------------------|--------------------------|----------------|
| 1 | $NEt_3$ | 28.2 | 1.4 | 81 |
| 4 | $NEt_2Me$ | 24.4 | 2.2 | 90 |
| 5 | $NEtMe_2$ | 20.4 | 1.6 | 87 |
| 6 | $NMe_3$ | 19.5 | 0.7 | 74 |
| 7 | DABCO | 15.6 | 1.1 | 52 |
| 8 | DBN | 25.3 | 0.4 | 99 |
| 9 | DBU | 42.2 | 0.3 | 89 | h = hours
kg = kilograms
DABCO is 1,4-Diazabicyclo [2.2.2] octane
DBN is 1,5-Diazabicyclo [4.3.0] non-5-ene
DBU is 1,8-Diazabicyclo [5.4.0]undec-7-ene

EXAMPLES 10-12

These examples show that a range of isopropanol/water mixtures may be used.

The method of Example 1 was followed and the autoclave charged with 101.5 g of isopropanol, 28.2 g of triethylamine and rhodium trichloride, triphenylphosphine and water in the amounts given in Table 2. The rates of reaction and conversion to the appropriate formate salt, for each example are given in Table 2.

TABLE 2

| Example No. | % Isopropanol (molar) in Isopropanol/Water Mixture | Rhodium Trichloride | Triphenyl-Phosphine (g) | Water (g) | Reaction Rate (mol/kg/hr) | Conversion (%) |
|-------------|-----|-------|-------|------|-----|----|
| 10 | 40 | 0.179 | 0.537 | 45.7 | 1.7 | 81 |
| 11 | 50 | 0.163 | 0.491 | 30.4 | 1.7 | 77 |
| 1  | 60 | 0.153 | 0.457 | 19.5 | 1.4 | 81 |
| 12 | 80 | 0.140 | 0.421 | 7.6  | 0.5 | 67 |

EXAMPLE 13

The method of Example 1 was followed with the exception that the reaction temperature was 80° C. instead of 40° C. The rate of reaction and conversion to triethylammonium formate were 4.3 mol/kg/h and 39% respectively.

EXAMPLE 14

This example shows that the unpromoted ruthenium catalysts described in our European Application No. 83 302945.9 have lower productivities than the catalysts described herein.

The method of Example 1 was followed except that the autoclave was charged with 101.6 g of isopropanol, 19.5 g of water, 28.3 g of triphenylphosphine and 0.137 g of $[Ru(CO)_2Cl_2]_n$. The rate of reaction and conversion to triethylammonium formate were 0.15 mol/kg/h and 78% respectively.

EXAMPLE 15

This example shows that a solvent system comprising mixed alcohols and water may be employed.

A 100 ml capacity stainless steel autoclave was charged with 34.2 g of isopropanol, 6.5 g of water, 0.214 g of tris(triphenylphosphine) rhodium (I) chloride, 9.7 g triethylamine and 8.9 g of tetraethylene glycol $[O(CH_2CH_2OCH_2CH_2OH)_2]$. The autoclave was closed and carbon dioxide was introduced until a steady pressure of 27 bar was reached. Hydrogen was introduced to give an initial total pressure of 80 bar, and the reactor heated to 80° C. After 0.5 hours the autoclave was cooled and the excess pressure discharged in this example the rate of reaction and conversion to triethylammonium formate were 5.5 mol/kg/h and 63% respectively.

EXAMPLE 16

This example, which does not constitute part of the invention, shows that when rhodium is used in the absence of the organophosphorus component no reaction occurs.

A 300 ml capacity stainless steel autoclave, fitted with a rotary stirrer, was charged with 101.5 g of isopropanol, 19.7 g water, 28.2 g triethylamine and 0.152 g rhodium trichloride. The autoclave was closed and carbon dioxide was introduced until a steady pressure of 27 bar was reached. The autoclave was then heated to 40° C. and hydrogen introduced to give an initial total pressure of 80 bar. After 1.5 hours the autoclave was cooled to room temperature and the excess pressure discharged. A sample of the liquid reaction product was then taken and treated with 5M hydrochloric acid. No formic acid was detected by gas-liquid chromatography.

I claim:

1. A process for the production of a formate salt of a nitrogenous base containing a tertiary nitrogen atom which process comprises reacting hydrogen and carbon dioxide with the nitrogenous base containing a tertiary nitrogen atom in the presence of a solvent and an effective amount of a catalyst characterised in that the catalyst comprises an inorganic or organometallic compound of rhodium and an organophosphorus compound.

2. A process as claimed in claim 1 characterised in that the nitrogenous base containing a teritary nitrogen atom is a lower trialkylamine.

3. A process as claimed in claim 2 characterised in that the lower trialkylamine is selected from the group comprising trimethylamine, triethylamine, tri-n-propylamine and trin-n-butylamine.

4. A process as claimed in claim 1 characterised in that the solvent is a mixture of one or more alcohols with water.

5. A process as claimed in claim 4 characterised in that the alcohol is a secondary alcohol or a glycol.

6. A process as claimed in claim 1 characterised in that the organophosphorus compound is a phosphine.

7. A process as claimed in claim 6 characterised in that the phosphine is either triphenylphosphine or tri-n-butylphosphine.

8. A process as claimed in claim 1 characterised in that the formate salt of the nitrogenous base containing a tertiary nitrogen atom is separated from the reaction mixture.

9. A process for the production of a formate salt of a nitrogenous base containing a tertiary nitrogen atom which process comprises reacting hydrogen and carbon dioxide with the nitrogenous base containing a tertiary nitrogen atom in the presence of a solvent and an effective amount of a catalyst characterized in that the catalyst is selected from the group consisting of
 (A) an inorganic or organometallic compound of rhodium and an organophosphorus compound selected from the group consisting of tri-n-butylphosphine, triphenylphosphine, tricyclohexylphosphine, 1,2-diphenylphosphinoethane and $CH_3C(P(C_6H_5)_2)_3$; and
 (B) the phosphine complex of rhodium which is tris(triphenylphosphine) rhodium chloride.

10. The process of claim 9, wherein the rhodium compound of (A) is a rhodium halide.

11. The process of claim 9, wherein the rhodium compound of (A) is rhodium trichloride.

12. The process of claim 1, wherein the organophosphorus compound is selected from the group consisting of tri-n-butylphosphine, tricyclohexylphosphine, 1,2-diphenylphosphinoethane and $CH_3C(P(C_6H_5)_2)_3$.

13. The process of claim 9, wherein the organophosphorus compnd is selected from the group consisting of tri-n-butylphosphine, tricyclohexylphosphine, 1,2-diphenylphosphinoethane and $CH_3C(P(C_6H_5)_2)_3$.

14. The process of claim 1, which is operated at a temperature between 15° C. to 40° C.

15. The process of claim 9, which is operated at a temperature between 15° C. to 40° C.

* * * * *